United States Patent [19]

Cox

[11] 4,193,986
[45] Mar. 18, 1980

[54] FLEA COMPOSITION FOR ANIMALS

[76] Inventor: Nicholas D. Cox, South Rte., P.O. Box 12, Lavina, Mont. 59046

[21] Appl. No.: 941,217

[22] Filed: Sep. 11, 1978

[51] Int. Cl.$^2$ ............... A01N 17/00; A01N 9/02; C11D 9/50; A01K 27/00
[52] U.S. Cl. ............... 424/28; 424/195; 424/DIG. 10; 119/106; 252/107
[58] Field of Search ............... 424/195, 28, DIG. 10; 252/107

[56] References Cited

U.S. PATENT DOCUMENTS

| | | | |
|---|---|---|---|
| 173,945 | 2/1876 | Hall et al. | 424/195 |
| 279,852 | 6/1883 | Atkins | 424/195 |
| 351,897 | 11/1886 | Boyer | 424/195 |
| 901,083 | 10/1908 | Ellis | 424/195 |

OTHER PUBLICATIONS

J. Econ. Entomol. 39, pp. 767–769 (1946).
The Drug and Cosmetic Industry, Feb. 1941 : 48,2, pp. 149, 150, 151 & 165.
The Pharmaceutical Recipe Book, First Edition, Pub. by The Amer. Pharm. Assoc. (1929), pp. 389 & 390.
Steinmetz, Codex Vegetabilis (1957).

*Primary Examiner*—Donald B. Moyer
*Attorney, Agent, or Firm*—Arthur L. Urban

[57] ABSTRACT

A natural composition for the flea treatment of animals comprising an inert vehicle and between about 2% and 7% by weight active ingredients consisting essentially of between about 10 and 40 parts oil of pennyroyal, between about 5 and 20 parts oil of eucalyptus, between about 3 and 10 parts cedar oil, between about 3 and 10 parts oil of citronella, and between about 1 and 2 parts oil of rue.

13 Claims, No Drawings

FLEA COMPOSITION FOR ANIMALS

This invention relates to a novel composition for the flea treatment of animals and more particularly relates to a new formulation of natural ingredients for animal flea treatment.

Flea infestation of mammels has been a problem through the ages. While improvements in hygiene and sanitation have eliminated the flea problem for human beings in most parts of the world, household pets and domestic animals still are subject to flea infestation. The problem is especially apparent to owners of household pets such as cats and dogs since these animals often have a great deal of contact with their owners.

Pet owners spend large sums each year on pet care. One of the major expenditures is in the area of flea treatments. A variety of products are commercially available for flea treatment including shampoos, sprays, powders and the like. A serious limitation of such products is the short time period in which they are effective. This limit on their effectiveness means that the flea treatment must be repeated frequently in order to prevent reinfestation.

The problem of reinfestation is particularly significant with dogs. Although the dog's fleas may have been eliminated from the body of the pet and his surroundings, when the dog is exercised away from his houshold he is in an uncontrolled environment. During these exercise periods, which may be on a daily basis, the dog often comes into contact with other dogs whose owners are not conscientious about keeping their pets free of fleas. Since only minimum contact is required for transfer of fleas, a pet may be reinfested easily.

More recently, flea collars and tags have been offered as a means of providing continuous protection against fleas. The collar or tag is impregnated with a preparation which is released at a controlled rate over an extended time period. Fleas require moisture daily and ordinarily migrate over the animal's neck to its mouth for the moisture. During these movements, the fleas pass close to the treated collar and receive a fatal dose of the flea preparation.

An important concern of pet owners is the hazardous character of the chemicals used in the flea treatment. Not only is the owner concerned about the effect such chemicals will have on the health of his pet, but also the effect of such chemicals on the health of the members of his family who are in contact with the pet. While it may be possible for adults to minimize their exposure, it is very difficult for pet owners to control the actions of their children in this respect. It is virtually impossible for parents to supervise their children's contact with their pets. Even if it were possible, such measures would interfere with the development of a good relationship between the children and the pet. The development of such a relationship frequently is the primary reason for owning a pet in the first place.

Thus, the pet owner is faced with the dilemma of whether to remove the chemicals from the body of the pet after the treatment to reduce the hazard created by the continuing presence of the chemicals. The alternative is to allow the residual chemicals to remain on the pet and exercise greater care in administering the flea treatment to his pet and minimizing contact of human beings with the pet to reduce exposure to the chemicals. In view of this situation, pet owners are still seeking a flea treatment for their animals that eliminates fleas and provides protection against reinfestation and yet is not hazardous to the pet and/or persons coming into contact with the pet.

The present invention provides a novel composition for the flea treatment of animals and particularly household pets. The flea composition of the invention is formulated of natural ingredients. Furthermore, the composition is easily formulated with commercially available materials using conventional mixing techniques. Also, the flea composition of the invention is relatively inexpensive.

Other benefits and advantages of the novel flea composition of the present invention will be apparent from the following description.

The natural composition for the flea treatment of animals of the present invention comprises an inert vehicle and between about 2% and 7% by weight of active ingredients consisting essentially of between about 10 and 40 parts oil of pennyroyal, between about 5 to 20 parts oil of eucalyptus, between about 3 and 10 parts cedar oil, between about 3 and 10 parts oil of citronella, and between about 1 and 2 parts oil of rue.

Preferably, the active ingredients consist essentially of between about 17 and 32 parts oil of pennyroyal, between about 8 and 16 parts oil of eucalyptus, between about 5 and 8 parts cedar oil, between about 5 and 8 parts oil of citronella, and between about 1.25 and 1.75 parts oil of rue; totalling 3 and 6%.

The oil of pennyroyal employed in the flea composition of the inventin is a volatile oil from the leaves and flowering tops of hedeoma or squaw mint. The oil which is chiefly pulegone is a pale yellow liquid with an aromatic odor between peppermint and camphor.

The oil of eucalyptus utilized in the composition of the invention is a volatile oil from the fresh leaves of various eucalyptus species. The oil is colorless to pale yellow liquid with a camphoraceous odor and consists chiefly of eucalyptol or cineol.

The cedar oil employed in the composition of the invention is a volatile oil from the wood of various cedar species. The oil consists primarily of cedene, a terpene, and is a colorless or slightly yellow somewhat viscous liquid.

The oil of citronella in the composition of the invention is a volatile oil from fresh grass of cymbopogon species. The oil is a light yellow liquid including citronellol and geraniol as principal constituents.

The oil of rue employed in the composition of the invention is a volatile oil of ruta species. The oil consists chiefly of methylnonylketone and is a pale yellow liquid with a sharp unpleasant odor which becomes pleasant on dilution.

The inert vehicle utilized in the composition of the invention will depend upon the particular use or application for the composition. For example, the composition may be incorporated into a soap, spray or the like where the inert vehicle may include a soap base, an aqueous emulsion, an organic solvent, etc. Compositions including inert vehicles such as petrolatum, paraffin wax and mixtures thereof are especially useful as impregnants in products such as flea collars, mats, blankets, etc. Flea collars utilizing a natural fibrous material such as a cotton rope or cord, are particularly advantageous. Preferred inert vehicles as shown above are oleaginous materials. Other examples of such materials are solid or liquid natural materials e.g. animal or vegetable oils or fats.

The composition of the present invention is easily formulated. Since the active ingredients all are liquids, the oils simply are combined and mixed. The resulting mixture then is added to the inert vehicle. If the inert vehicle is not a liquid, e.g. a wax, jelly, soap, etc., the vehicle may be heated to liquify it prior to the addition of the oil mixture.

In the fabrication of animal products such as collars, mats, blankets, etc., it is desirable to achieve good adhesion of the composition to the base material. Dipping of the base material into a liquified composition is especially useful with collars since it provides a high degree of penetration. Good penetration gives a longer effective life to the treated product. If the product does not lend itself to dipping e.g. in the case of quilted mats, the mat may be coated with the composition of the invention.

The above description shows that the present invention provides a novel formulation for the treatment of flea infested animals and especially the treatment of household pets. The composition of the invention is easily formulated from natural ingredients which are commercially available. Conventional mixing techniques may be employed in the formulation of the composition. The composition of the invention is particularly useful in the fabrication of flea collars although it can be utilized to treat or be incorporated into other products such as soaps, sprays or wipe-on liquids and the like. In addition, the composition can be used to treat products and articles with which the pet has contact, for example, mats, rugs, blankets and the like. In each case, the composition provides a formulation of natural ingredients for the treatment of flea infested pets.

It will be apparent that various modifications can be made in the particular formulation described in detail above within the scope of the invention. For example, other ingredients may be incorporated in the formulation provided they do not have a deleterious effect on the performance characteristics of the composition of the invention. It may be desirable in some applications to change the odor, color, viscosity or other aspects of the composition. In addition, the inert vehicle may be different to meet specific requirements, e.g. a powder. Therefore, the scope of the invention is to be limited only by the following claims.

What is claimed is:

1. A composition for the treatment of flea infested animals comprising an inert vehicle and between about 2% and 7% by weight of natural active ingredients consisting essentially of between about 10 and 40 parts oil of pennyroyal, between about 5 and 20 parts oil of eucalyptus, between about 3 and 10 parts cedar oil, between about 3 and 10 parts oil of citronella, and between about 1 and 2 parts oil of rue.

2. A composition according to claim 1 wherein said natural active ingredients comprise between about 3% and 6% of said composition and consist essentially of between about 17 and 32 parts oil of pennyroyal, between about 8 and 16 parts oil of eucalyptus, between about 5 and 8 parts cedar oil, between about 5 and 8 parts oil of citronella, and between about 1.25 and 1.75 parts oil of rue.

3. A composition according to claim 1 wherein said inert vehicle is an oleaginous material.

4. A composition according to claim 1 wherein said inert vehicle includes a major proportion of paraffin wax.

5. A composition according to claim 1 wherein said inert vehicle includes petrolatum.

6. A composition according to claim 4 wherein said composition includes petrolatum.

7. A composition according to claim 1 wherein said inert vehicle is a soap.

8. A composition according to claim 1 wherein said inert vehicle is an aqueous emulsion.

9. A composition according to claim 1, wherein said inert vehicle is an organic solvent.

10. An animal collar treated with the composition of claim 1.

11. A mat treated with the composition of claim 1.

12. The animal collar according to claim 10 wherein said composition is applied to a cotton rope.

13. A composition according to claim 1 wherein said natural active ingredients comprise about 4% of said composition and consist essentially of about 24 parts oil of pennyroyal, about 12 parts oil of eucalyptus, about 6 parts cedar oil, about 6 parts oil of citronella, and about 1.5 parts oil of rue.

* * * * *